United States Patent
Haese et al.

(10) Patent No.: US 7,132,576 B2
(45) Date of Patent: *Nov. 7, 2006

(54) METHOD FOR ISOMERIZING ALLYL ALCOHOLS

(75) Inventors: Frank Haese, Lambsheim (DE); Klaus Ebel, Lampertheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 7 days.

This patent is subject to a terminal disclaimer.

(21) Appl. No.: 10/497,523

(22) PCT Filed: Dec. 4, 2002

(86) PCT No.: PCT/EP02/13690

§ 371 (c)(1), (2), (4) Date: Jun. 3, 2004

(87) PCT Pub. No.: WO03/047749

PCT Pub. Date: Jun. 12, 2003

(65) Prior Publication Data

US 2005/0101807 A1    May 12, 2005

(30) Foreign Application Priority Data

Dec. 7, 2001 (DE) ................. 101 60 147

(51) Int. Cl.
*C07C 35/00* (2006.01)
*C07C 29/00* (2006.01)

(52) U.S. Cl. ............ 568/875; 568/906; 502/167; 556/57; 546/2

(58) Field of Classification Search ........ 568/875, 568/906; 502/167; 556/57; 546/2
See application file for complete search history.

(56) References Cited

U.S. PATENT DOCUMENTS

| | | | |
|---|---|---|---|
| 6,054,407 A | 4/2000 | Schulz et al. | |
| 2004/0097765 A1* | 5/2004 | Haese et al. | 568/906 |
| 2005/0070745 A1* | 3/2005 | Haese et al. | 568/875 |

FOREIGN PATENT DOCUMENTS

| | | |
|---|---|---|
| DE | 25 16 698 | 10/1975 |
| DE | 195 33331 | 3/1997 |
| DE | 10046865 A1 * | 3/2002 |
| GB | 1 256 184 | 12/1972 |
| WO | 01/42177 | 6/2001 |

OTHER PUBLICATIONS

Rice, Inorg. Chem., vol. 20, pp. 1996-2000 (1981).*
Tetrahedron 33, 1977, 1775-1783, Chabardes et al.
European Journal of Inorganic Chemistry, 1999, (2), 313-321, Wong et al.
Journal of Organometallic Chemistry, 2000, 603(1), 69-79, Herrmann et al.
Chem. Letters, Chemical Soc. of Japan, Tokyo, Nr. 3, 1982, 357-360, Hosogai et al.

* cited by examiner

Primary Examiner—Rosalynd Keys
(74) Attorney, Agent, or Firm—Novak Druce & Quigg, LLP

(57) ABSTRACT

The present invention relates to a process for isomerizing reactant allyl alcohols of the formula (I) to product allyl alcohols of the general formula (II)

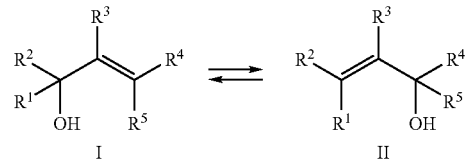

where R1 to R5 are each hydrogen or a mono- or polyunsaturated or saturated $C_1$–$C_{12}$-alkyl radical, which can be substituted or unsubstituted,
in both directions of the equilibrium, which comprises isomerizing in the presence of a dioxotungsten(VI) complex of the general formula (III),

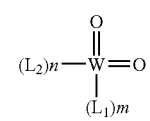

(III)

where
$L_1$, $L_2$ are each independently a ligand selected from the group consisting of the aminoalcohols, the aminophenols and mixtures thereof,
m, n are each 1 or 2, new dioxotungsten(VI) complexes, and also their use.

9 Claims, No Drawings

METHOD FOR ISOMERIZING ALLYL ALCOHOLS

The present invention relates to a process for isomerizing reactant allyl alcohols to product allyl alcohols in both directions of the equilibrium, which comprises isomerizing in the presence of a dioxotungsten(VI) complex, and also to novel dioxotungsten(VI) complexes and their use.

Allyl alcohols are important intermediates in industrial organic product synthesis. Tertiary allyl alcohols in particular are used for example as intermediates in the preparation of scents in their own right or else as additives in soaps and detergents.

Allyl alcohols isomerize under acid catalysis. This isomerization corresponds to a 1,3-migration of the hydroxyl group and an internal shift of the double bond, as is shown in the following equation with the general formulae I and II:

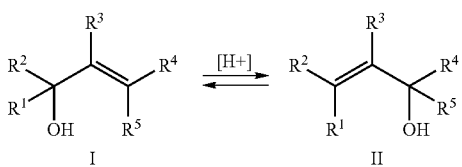

where R1 to R5 are each hydrogen or a mono- or polyunsaturated or saturated $C_1$–$C_{12}$-alkyl radical, which can be substituted or unsubstituted.

The process is particularly suitable for the preparation of tertiary product allyl alcohols, such as 2-linalool, by isomerization of primary or secondary allyl alcohols, such as geraniol or nerol.

Geraniol (2-trans-3,7-dimethyl-2,6-octadien-8-ol), nerol (2-cis-3,7-dimethyl-2,6-octadien-8-ol) and 2-linalool (3,7-dimethyl-1,6-octadien-3-ol) are important compounds in the scent industry. They are used either directly as scents or converted to scents of higher molecular weights by reaction with other compounds. These terpene alcohols are also important as $C_{10}$ building blocks in the synthesis of vitamins, such as vitamin E and vitamin A.

In the past, the literature preferentially described processes for the isomerization of linalool to geraniol. Since isomerizations are equilibrium reactions, the processes developed are in principle also usable for the reverse reaction of isomerization of geraniol or nerol to give linalool.

Initially, isomerization reactions of allyl alcohols were carried out using acids as catalysts. However, these processes were only of limited importance, since they were dominated by side reactions, such as dehydration or cyclization.

Later, molybdenum, vanadium and tungsten compounds were identified as catalysts for the rearrangement of substituted allyl alcohols and investigated as such (cf. P. Chabardes et al. in *Tetrahedron* 33 (1977), 1775–1783).

While the molybdenum compound described as an isomerization catalyst in GB 125 6184 gave unsatisfactory reaction results, relatively high selectivities coupled with simultaneously higher activities were possible using the tungstenoxo(VI) alkoxide catalysts of the formula WO(OR)$_4$ in the presence of a nitrogen base as an additional ligand than were possible using the analogous vanadiumoxo(V) alkoxide catalysts of the formula VO(OR)$_3$. Further advantages of the tungsten catalysts are that they can firstly be easily separated from the reaction mixture (cf. T. Hosogai et al. in *Chemistry Letters* 1982, pages 357–360) and, secondly, that they only have a low toxicity compared to the vanadium catalyst.

Furthermore, DE 25 16 698 discloses the preparation of novel catalysts based on tungsten, and also their use for the catalytic rearrangement of tertiary allyl alcohols to give primary allyl alcohols. Suitable catalysts described for this process include tungstenoxo(VI) complexes containing alkoxy radicals and/or trialkylsilyl radicals attached through oxygen, which lead to an improvement in the selectivity for ligands additionally coordinated to the tungsten, which contain an element selected from the group consisting of N, P, As and Bi, in particular ligands selected from the group consisting of the primary, secondary and tertiary monoamines, the polyamines, the Schiff bases, the imines, nitriles and isonitriles. Particularly suitable ligands mentioned therein include primary monoamines, such as methylamine, ethylamine, propylamine, β-ethoxyethylamine, butylamine, cyclohexylamine, aniline and naphthylamine; secondary monoamines, such as dimethylamine, diethylamine, dibutylamine, dicyclohexylamine, methylaniline, methylcyclohexylamine, piperidine, morpholine and pyrrolidine; tertiary monoamines, such as trimethylamine, triethylamine, ethyldibutylamine, tricyclohexylamine, dimethylaniline, pyridine, picoline, quinoline, isoquinoline, N-methylpyrrolidine and N-methylmorpholine; ethylenediamine, pyrazine, piperazine, pyrimidine, triethylenediamine, 1,8-diazabicyclo[5.4.0]undec-7-ene, polyethyleneimines, and also ion exchange resins having a multiplicity of amino groups within the molecule, in particular pyridine, triethylamine, cyclohexylamine, diethylamine and tricyclohexylphosphine. Aminoalcohols are not mentioned therein.

Our investigations into the isomerization of geraniol using a 0.05 mol % solution of tungstenoxo(VI) tetrakisgeranylate by a process similar to that described in DE 25 16 698 showed that the rearrangement of linalool in the presence of a nitrogen base at 200° C. (reaction time about 1 hour) is much more selective than when a nitrogen base is not used. Suitable nitrogen bases here include diethylamine, pyridine, imidazole and poly-(4-vinylpyridine). Improvements were achieved by the addition of aminoalcohols to the catalyst solution (see comparative experiments, examples 2 to 6). The selectivities for linalool obtained using this process are very good, but the conversions obtained leave a lot to be desired.

So the comparatively low conversions coupled with simultaneously high temperatures of over 150° C., which accelerated the formation of byproducts, had a disadvantageous effect in these experiments.

DE 25 16 698 also describes the synthesis of tungsten alkoxides, by alcoholysis of tungstenoxo tetrachloride using alcohols or alcoholic solutions of alkoxides. Although the removal of the chloride in the form of ammonium chloride using ammonia or as sodium chloride using sodium methoxide is possible, it is always incomplete. Chlorine is also almost always present in the distilled allyl alcohol product, which strongly compromises its quality and acceptability for use in scents and vitamins. Additionally, even ppm quantities of chloride in tungsten alkoxides can have adverse corrosive effects in metal columns and reactors. Subsequent removal of chloride traces using activated carbon filters or silver(I) oxide is possible but inconvenient and makes the complete process complex and more expensive.

Further, tungstenoxo tetrachloride has to be prepared by known methods using tungstic acid and thionyl chloride in a preceding reaction, so that the synthesis of tungsten alkoxides has to be carried out at high expense in a multistep process.

The process for the preparation of tungstenoxo(VI) alkoxide complexes that is similarly described in DE 25 16 698, starting from tungsten trioxide and hydroxy compounds, is not usable in industrial scale applications because of the poor yields.

Tungsten alkoxides are known to be sensitive to hydrolysis and react with water to give alcohols and tungsten oxide. Since dehydration always occurs as a side reaction of allyl alcohol isomerization, sparingly soluble tungsten oxides precipitate increasingly out of the reaction mixture under the conditions of allyl alcohol isomerization. These increase the catalyst costs and further support the formation of byproducts, and also water from allyl alcohols, and lead to further deterioration in selectivity.

It is an object of the present invention to provide further improvements in the process of isomerization of allyl alcohols such that the tungstenoxo catalyst can be prepared halogen-free and using simple, inexpensive steps, in order to avoid contamination of allyl alcohol with halogen, and further to avoid corrosion problems in the plant. Furthermore, the catalyst losses resulting from hydrolysis should be reduced or totally avoided and the product selectivity should be improved. The need also exists to speed equilibration and to increase the space-time yields without having to further increase the isomerization temperature.

Furthermore, the improved catalysts should achieve higher conversions of the reactant allyl alcohol from the isomerization of primary or secondary allyl alcohols, such as geraniol or nerol, to give tertiary allyl alcohols, such as linalool, i.e. speed equilibration. Also, the new catalysts should be easier to prepare than their predecessors.

We have found that this object is achieved by novel homogeneously dissolved dioxotungsten(VI) complexes of the general formula (III), with simultaneously improved selectivity and higher activity for the isomerization of geraniol and nerol to give linalool.

According to the invention, homogeneous solutions of dioxotungsten(VI) in water, alcohol or a different solvent can be used.

The invention provides a process for isomerizing reactant allyl alcohols of the formula (I) to product allyl alcohols of the general formula (II)

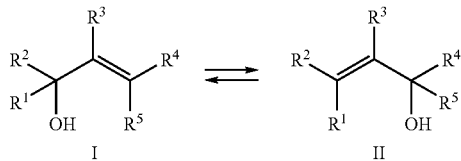

where R1 to R5 are each hydrogen or a mono- or polyunsaturated or saturated $C_1$–$C_{12}$-alkyl radical, which can be substituted or unsubstituted, in both directions of the equilibrium, which comprises isomerizing in the presence of a dioxotungsten(VI) complex of the general formula (III),

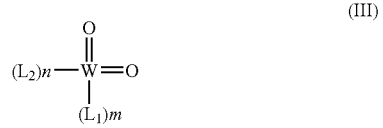

where $L_1$, $L_2$ are each independently a ligand selected from the group consisting of the aminoalcohols, the aminophenols and mixtures thereof, m, n are each 1 or 2.

The following allyl alcohols of the general formula (I) or (II) can be advantageously isomerized by means of the process of the invention: 2-methyl-3-buten-2-ol, prenol (3-methyl-2-buten-1-ol), linalool, nerol and geraniol, and also farnesol (3,7,11-trimethyldodeca-2,6,10-trien-1-ol) and nerolidol (3,7,11-trimethyldodeca-1,6,10-trien-3-ol), in particular linalool, nerol and geraniol.

The ligands L1 and/or L2 can be either ligands such as aminoalcohols, aminophenols or mixtures thereof.

Examples of suitable aminoalcohols include: triethanolamine, diethanolamine, monoethanolamine, tripropanolamine, dipropanolamine, 3-amino-1-propanol, 1-amino-2-propanol, 2-amino-1-propanol, butyldiethanolamine, methyldiisopropanolamine, N-(2-hydroxybenzyl) amine or N,N'-bis-(2-hydroxy-benzyl)-1,2-diaminoethane, α,α-diphenyl-L-prolinol, L-tryptophanol, L-alaninol, L-isoleucinol, L-leucinol, L-methioninol, L-phenylalaninile, L-valinol and 2-(2-pyridyl)propan-2-ol.

Examples of suitable aminophenols include: o-aminophenol, m-aminophenol, p-aminophenol, or 8-hydroxyquinoline unsubstituted or substituted by halogen, alkyl, amino, hydroxy, alkoxy, thio, sulfonyl or nitro, 3-amino-2-naphthol, N-methyl-2-aminophenol, N,N-dimethyl-2-aminophenol, 2-piperidinophenol, 2-hydroxypyridine, N-methyl-2,2'-imino-bis(8-hydroxyquinoline), particularly preferably 8-hydroxyquinoline.

The phenols can be unsubstituted or substituted by halogen, alkyl, amino, hydroxyl, alkoxy, thio, sulfonyl or nitro.

The addition of ammonia or else amines to the reactant allyl alcohol, or else to the catalyst solution is advantageous.

Suitable amines include, for example, mono-, di- or trimethylamine, ethylamine, mono-, di- or triethylamine, mono-, di- or tributylamine, preferably diethylamine.

Suitable alcohols include, unless otherwise stated, any alcohol ROH, where R is a mono- or polyunsaturated or saturated $C_1$–$C_{15}$-alkyl radical, which is substituted by one or more of the substituents selected from the group consisting of halogen, $C_1$–$C_6$-alkyl, amino and hydroxyl, for example methanol, ethanol, propanol, isopropanol, butanol, tert-butanol, pentanol, geraniol, nerol, nerolidol, prenol, linalool or farnesol.

The invention further provides novel dioxotungsten(VI) complexes of the general formula (III),

where $L_1$, $L_2$, n and m are each as defined above.

Particularly preferred complexes are those in which the ligands L1 and/or L2 are each 8-hydroxyquinoline.

The molar ratio of tungsten to 8-hydroxyquinoline is in the range from 1:1 to 1:5, preferably from 1:1 to 1:2, and is particularly preferably 1:2.

The molar ratio of tungsten to 8-hydroxyquinoline in the solution of the complex is at least 1:1. Molar ratios of greater than 1:7 are also possible but do not yield any further benefit.

The dioxotungsten(VI) complexes can be obtained using the corresponding oxoperoxotungsten(VI) complex as an intermediate.

According to the process described in DE 195 33 331, the oxoperoxotungsten(VI) complex is initially prepared from tungstic acid and an aqueous hydrogen peroxide solution with optional subsequent addition of the ligand or ligands. This is then reduced to give the tungstenoxo compound.

Suitable reducing agents include the reactant allyl alcohol itself or, for example, sodium thiosulfate or iron(II) salts, but in particular geraniol and/or nerol.

However, the dioxotungsten(VI) complex can also be prepared from tungsten(VI) dioxo dichloride without the addition of a reducing compound.

The dioxotungsten(VI) complex can either be prepared separately before the actual reaction or in situ in the reactant allyl alcohol.

In general, the dioxotungsten(VI) complex is dissolved in the reactant allyl alcohol in a concentration in the range from 0.001 to about 5% by weight.

It is particularly advantageous first to combine the ligand L1 or L2 with or without an additional organic solvent with the aqueous or organic solution of the dioxotungsten(VI) complex and only then to add the thus prepared solution or suspension of the finished catalyst to the reactant allyl alcohol. The additional ligands are generally used in a quantity in the range from 1 mol % to 1000 mol %, preferably from 100 mol % to 700 mol %, relative to the tungsten quantity. Larger ligand quantities are also possible, but result in no further advantage.

The absolute concentrations of ligand and tungsten complex in the reaction mixture are not critical in the process of the invention and can, for example, be increased such that the speed at which equilibrium is achieved can be increased as desired.

An increase in the speed at which equilibrium is achieved can also be achieved in the process of the invention by removing water formed by side reactions from the mixture, for example by passing an inert gas stream over, the addition of known water-removing agents or stripping with the product allyl alcohol gas stream during distillation.

The process of the invention is generally carried out at from 50 to 300° C., preferably from 150 to 250° C.

It can be carried out either with or without the use of a solvent, batchwise, but also continuously. Suitable solvents include organic solvents such as toluene, tetrahydrofuran, benzene, cyclohexane, xylene, methylene chloride or mesitylene, but preferably the reactant allyl alcohol itself is used as the solvent.

The process of the invention is advantageous when the reactant allyl alcohol is present in the reaction mixture in a concentration in the range from about 10 to 100% by weight.

The process of the invention is particularly advantageous when the reactant allyl alcohols used are geraniol and nerol and the produkt allyl alcohol is 2-linalool.

To work up, 2-linalool is removed from the product mixture by distillation, as a lower-boiling component. In general, reactant allyl alcohols and secondary compounds will be present in the product allyl alcohol. Distillation to obtain the pure product allyl alcohol can be carried out by known methods.

Isomerization is an equilibrium reaction and the location of the equilibrium depends on the thermodynamic properties of the reactant and product allyl alcohols, and also on the reaction conditions. Continuous or batchwise separation of linalool, the lowest-boiling allyl alcohol, from the reaction mixture using the base of the distillation column as the reaction chamber, allows a favorable space-time yield to be achieved because of the shifting of the equilibrium even in the case of unfavorable equilibration.

The following examples illustrate the invention:

Preparation of a cis-dioxotungsten(VI) Complex Using the Example of cis-dioxotungsten(VI) bis(oxinate)

EXAMPLE 1

Tungstic acid is suspended, for example, at 40° C. in a 3.5:1 excess of aqueous hydrogen peroxide. After stirring for 6 hours, the solution is filtered. 8-Hydroxyquinoline is added to this prepared oxoperoxotungsten(VI) solution. The 8-hydroxyquinoline is added in solid form or as a melt, or added dropwise dissolved in an organic solvent, e.g. an alcohol. 8-Hydroxyquinoline is preferably added in a quantity of from 1 to 3.5 mol equivalents relative to tungsten. The solution or suspension obtained is used directly for the isomerization of a reactant allyl alcohol, by adding it to geraniol and/or nerol. The oxoperoxotungsten(VI) complex reacts with the reactant allyl alcohol to give cis-dioxotungsten(VI) complex and geraniol and/or nerol epoxide. The mixture obtained can be used directly for further isomerization, but the cis-dioxotungsten(VI) complex with 8-hydroxyquinoline as the ligand can also be precipitated by cooling or concentration of the mixture. The precipitated catalyst powder is filtered off, washed and dried. Any water present in the catalyst solution can be removed by distillation or by addition of drying agents. The novel tungsten complex prepared by the process described above contains two oxo groups and 8-hydroxyquinoline as a further ligand and is characterized by hydroxyquinoline being deprotonated at the phenolic OH group and the ratio of tungsten to 8-hydroxyquinoline being 1:2.

This catalyst can be added to the reactant allyl alcohol at from 20 to 300° C., either dissolved in any solvent or as a solid.

EXAMPLE 2 cis-Dioxotungsten(VI) bis(oxinate) can also be prepared without the addition of a reducing compound.

For this purpose, 2.0 g of tungsten(VI) dioxo dichloride are mixed with 10 g of methanol and 2.1 g of 8-hydroxyquinoline in a 50 ml autoclave under 2 bar of ammonia gas and heated to 90° C. for 24 hours. After cooling, the solid is filtered off and washed with methanol. The filter cake is boiled twice, in each case with 50 g of 50% by weight aqueous methanol, and after cooling is filtered off again and washed with methanol. The remaining cis-dioxotungsten (VI) bis(oxinate) powder is dried in the airstream of a water suction pump.

The yield is 89%.

| Microanalysis: | C: 42.3%; O: 12.7%; N: 5.4%; H: 1.9%; W: 38%; Cl org.: 0.056%; Cl inorg.: 0.038% |
|---|---|

EXAMPLE 3

The catalyst powder prepared in example 1 is used directly for the isomerization of geraniol. 50 g of geraniol are heated to 180° C. under argon in a 100 ml three-necked flask fitted with a distillation bridge. 0.14 g of the dried catalyst powder is then added and the mixture is stirred at 180° C. for 1 hour. During the isomerization, no product is distilled off. After cooling, GC analysis of the liquid phase is carried out.

| GC analysis in area %: | geraniol: 57.35%; nerol: 4.45%; linalool: 35.20%; low boilers: 0.55%; citral: 0.18%; high boilers: 2.37% |

What is claimed is:

1. A process for isomerizing reactant allyl alcohols of the formula (I) to product allyl alcohols of the general formula (II)

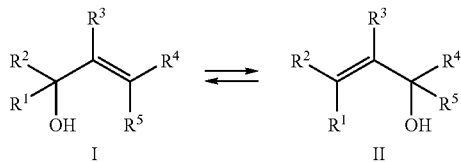

where R1 to R5 are each hydrogen or a mono or polyunsaturated or saturated C1–C12-alkyl radical, which can be substituted or unsubstituted,
in both directions of the equilibrium, which comprises isomerizing in the presence of a dioxotungsten(VI) complex of the general formula (III),

where
L1, L2 are each independently a ligand selected from the group consisting of the aminoalcohols, the aminophenols and mixtures thereof,
m, n are each 1 or 2.

2. The process as claimed in claim 1, wherein L1 and L2 are each 8-hydroxyquinoline.

3. The process as claimed in claim 2, wherein the ratio of tungsten to 8-hydroxyquinoline in the complex is in the range from 1:1 to 1:5.

4. The process as claimed in claim 1, wherein the ratio of tungsten to 8-hydroxyquinoline in the solution of the complex is at least 1:1.

5. The process as claimed in claim 1, wherein the allyl alcohols are selected from the group consisting of 2methyl-3-buten-2-ol, prenol (3-methyl-2-buten-1-ol), linalool, nerol, geraniol, farnesol (3,7,11-trimethyldodeca-2,6,10-trien-1-ol) and nerolidol (3,7,11-trimethyldodeca1,6,10-trien-3-ol).

6. The process as claimed in claim 1, wherein the reactant allyl alcohols are selected from the group consisting of geraniol and nerol.

7. The process as claimed in claim 1, wherein the dioxotungsten(VI) complex of the general formula (III) is prepared before the reaction or in situ in the reactant allyl alcohol.

8. The process as claimed in claim 1, wherein ammonia or an amine is added to the reactant allyl alcohol, to the catalyst or to a mixture of the reactant allyl alcohol and catalyst.

9. A process for isomerizing reactant allyl alcohols which comprises isomerizing the allyl alcohols in the presence of a dioxotungsten(VI) complex of the general formula (III)

where
L1, L2 are each independently a ligand selected from the group consisting of the aminoalcohols, the aminophenols and mixtures thereof,
m, n are each 1 or 2,
as catalyst.

* * * * *